(12) United States Patent
Bergmann

(10) Patent No.: US 7,915,002 B2
(45) Date of Patent: Mar. 29, 2011

(54) METHOD FOR CONTROLLING THE THERAPY OF PATIENTS SUFFERING FROM CARDIAC INSUFFICIENCY BY MEANS OF IN VITRO DETERMINATION OF THRESHOLD VALUES OF VASOACTIVE PEPTIDES

(75) Inventor: Andreas Bergmann, Berlin (DE)

(73) Assignee: B.R.A.H.M.S GmbH, Hennigsdorf (DE)

( * ) Notice: Subject to any disclaimer, the term of this patent is extended or adjusted under 35 U.S.C. 154(b) by 0 days.

(21) Appl. No.: 12/374,757

(22) PCT Filed: Jul. 18, 2007

(86) PCT No.: PCT/EP2007/006393
§ 371 (c)(1), (2), (4) Date: Apr. 29, 2009

(87) PCT Pub. No.: WO2008/012019
PCT Pub. Date: Jan. 31, 2008

(65) Prior Publication Data
US 2009/0311186 A1    Dec. 17, 2009

(30) Foreign Application Priority Data

Jul. 24, 2006  (DE) .......... 10 2006 034 142

(51) Int. Cl.
*G01N 33/53* (2006.01)
(52) U.S. Cl. .................. 435/7.1; 436/518
(58) Field of Classification Search .......... None
See application file for complete search history.

(56) References Cited

U.S. PATENT DOCUMENTS
2007/0212742 A1   9/2007  Bergmann et al.
2008/0026414 A1   1/2008  Bergmann et al.

FOREIGN PATENT DOCUMENTS
EP   1564558 B1   2/2004
EP   1619505 A2   1/2006
WO   2004/090546  10/2004
WO   2006/018315  2/2006

OTHER PUBLICATIONS

Schafer et al. (Basic Res Cardiol. 2002 vol. 97, p. 399-408).*
Written Opinion of the International Search Authority for corresponding PCT/EP2007/006393.
Joachim Struck et al., "Proteolytic processing pattern of the endothelin-1 precursor in vivo", Peptides 26 (2005) 2482-2486.
G. deGevigney et al., "Pathophysiology and therapeutic implications of left heart failure", Science Direct (2005) (Abstract Only).
Joachim Struck et al., "Identification of an Adrenomedullin precursor fragment in plasma of sepsis patients", Peptides 25 (2004) 1369-1372.
Albertus Beishuizen et al., "Circulating Cardiovascular Markers and Mediators in Acute Illness: an update", Clinica Chimica Acta 354 (2005) 21-34.
Nils G. Morgenthaler et al., "Measurement of Midregional Proadrenomedullin in Plasma with an Immunoluminometric Assay", Clinical Chemistry 51:10, (2005), 1823-1829.
Jana Papassotiriou et al., "Immunoluminometric Assay for Measurement of the C-Terminal Endothelin-I Precursor Fragment in Human Plasma", Clinical Chemistry 52:6, (2006), 1144-1151.
Nils G. Morgenthaler et al., "Assay for the Measurement of Copeptin, a Stable Peptide Derived from the Precursor of Vasopressin", Clinical Chemistry 52:1, (2006), 112-119.
Van Cheng et al., "A Rapid Bedside Test for B-Type Peptide Predicts Treatment Outcomes in Patients Admitted for Decompensated Heart Failure: A Pilot Study", Journal of American College of Cardiology, vol. 37(2), Feb. 2001, 386-91.
Kjaer A., "Neuroendocrine activation in heart insufficiency II. Can diagnosis be confirmed and prognosis evaluated by a blood test?", 2000.

* cited by examiner

*Primary Examiner* — Jacob Cheu
(74) *Attorney, Agent, or Firm* — Heslin Rothenberg Farley & Mesiti P.C.

(57) ABSTRACT

Disclosed is a method for controlling the therapeutic treatment of a patient suffering from cardiac insufficiency. In said method, it is determined how the concentration of at least one of the vasoactive peptides adrenomedullin (ADM), endothelin-1 (ET-1), and/or vasopressin (AVP) changes in the patient's blood after beginning the therapy, and the therapeutic measures are considered to be unsatisfactory and are modified in case said concentration does not decrease at all or not enough in relation to a threshold value for the respective vasoactive peptide.

13 Claims, No Drawings

METHOD FOR CONTROLLING THE THERAPY OF PATIENTS SUFFERING FROM CARDIAC INSUFFICIENCY BY MEANS OF IN VITRO DETERMINATION OF THRESHOLD VALUES OF VASOACTIVE PEPTIDES

CROSS REFERENCE TO RELATED APPLICATIONS

This application is a 371 filing of PCT International application no. PCT/EP2007/006393 filed Jul. 18, 2007 and published in German as WO 2008/012019 on Jan. 31, 2008, which claims the priority of German application no. 102006034142.2 filed Jul. 24, 2006. The disclosures of these applications and all other patents, published applications and other references cited herein are hereby incorporated by reference in their entirety.

The present invention relates to a novel application of a diagnostic in vitro method for determining certain vasoactive (acting on vessels; vasotropic) endogenous peptides in blood samples for controlling the therapy of patients suffering from cardiac insufficiency by assessing the success or failure of therapeutic interventions on the basis of the change in the measurable concentrations of such peptides.

The term cardiac insufficiency (heart failure, HF) is used when the heart is no longer capable of supplying the body adequately with blood and hence also with oxygen. Cardiac insufficiency (poor cardiac output) is not an independent disease but a clinical picture with various causes and a plurality of characteristic symptoms. Various terms are used for more precise characterization of various forms of cardiac insufficiency, depending on site of the disease, type of symptoms or type of development of the disease, of which in particular right-sided heart failure or left ventricular insufficiency (depending on whether the right side of the heart or the left side of the heart is diseased), global heart failure (advanced cases and/or if both chambers of the heart are primarily affected), systolic heart failure (the myocardial muscle is no longer able to pump vigorously), diastolic heart failure (the myocardial muscle can no longer correctly relax and fill with blood), forward and backward heart failure (insufficient blood output or backup of the blood before the heart), congestive heart failure (chf, decompensated right-sided heart failure), chronic heart failure (the symptoms develop slowly over months to years; a sudden acute deterioration is possible at any time) and acute heart failure (development of heart failure within minutes or hours, e.g. following a cardiac infarction) are to be mentioned in particular.

Cardiac insufficiency is due to poor pumping of the myocardium in 70% of cases, owing to coronary heart disease. It affects in particular the older population.

The classical diagnostic measures for detecting cardiac insufficiency are physical examinations of heart and lungs and for edema, ECG (also as exercise ECG and/or long-term ECG), blood pressure measurement, ultrasound examinations and, if appropriate, X-ray examinations, laboratory investigations, lung function tests and determination of the oxygen saturation of the blood. Depending on clinical and diagnostic findings, potential cardiac insufficiency patients and those suffering from cardiac insufficiency are assigned to four groups, particular on the basis of the recommendations of the New York Heart Association (NYHA) to the four so-called NYHA classes I to IV.

The following are applicable for assignment to the individual NYHA classes:

- NYHA I=no symptoms
- NYHA II=relatively vigorous physical activity results in symptoms (e.g. the shortness of breath after climbing 3 flights of stairs or on rapidly ascending a slope)
- NYHA III=light physical activity results in symptoms (e.g. shortness of breath after climbing 1 flight of stairs, on slowly ascending a slope or during rapid walking on the level)
- NYHA IV=symptoms experienced even at rest, which increase with light physical activity.

Recently, the measurement of endogenous vasoactive peptides, whose concentrations are changed in a characteristic manner compared with healthy control persons in the case of cardiac insufficiency, have increasingly also been used for diagnostic and prognostic purposes (so-called cardiovascular markers; cf. also (1)). In this context, the natriuretic peptides (ANP, BNP, CNP) and furthermore the vasoactive peptides adrenomedullin (ADM), endothelin-1 (ET-1) and vaso-pressin (arginine-vasopressin; AVP) may primarily be mentioned, the determination of which the present application is concerned with. The liberation of the last-mentioned three peptides was first measureable in a simple and valid manner with the aid of newly developed assays of the applicant which are explained in more detail below. It was found that high concentrations of AMP, ET-1 and AVP provide clear indications of a poor prognosis or a probably fatal outcome of the disease.

The basic therapy of a diagnosed chronic heart failure now includes in particular a treatment with ACE inhibitors (ACE—angiotensin converting enzyme), beta-blockers and in particular diuretics. Angiotensin-II receptor blockers (ARB), blood-thinning agents, calcium channel blockers, digitalis preparations (digitalis glycosides, such as, for example, digitoxin, digoxin and semisynthetic derivatives derived therefrom), vasodilators and measures such as increasing the potassium supply may be mentioned as further therapeutic agents used in the case of cardiac insufficiency. In severe cases (NYHA IV), so-called IV diuretics and, with a lower frequency, preparations such as dobutamine, dopamine, milrinon, nesiritide, nitroglycerine and nitroprusside are used. In the case of severe chronic or acute forms with imminent complications, such as pulmonary edema or a cardiogenic shock, the patients must be treated by intensive care owing to the critical prognosis.

A major part of the patients treated in the abovementioned context, however, respond only suboptimally to the standard therapies, with the consequence of the occurrence of "events" such as rehospitalization owing to severe symptoms (shortness of breath, circulatory failure) or death. It has been possible to date only with very great difficulty to detect the success or failure of a chosen treatment strategy at a sufficiently early stage that the therapeutic measures can, if appropriate, be changed in good time in the sense of a change of treatment before the abovementioned "events" occur owing to a lack of efficacy of the previously chosen therapeutic measures.

BNP has been and is being tested for use for therapy control but to date without convincing success (5).

It is therefore an object of the present invention to provide the physician with novel diagnostic possibilities which give clear indications as early as possible of the success of the treatment measures chosen for treating a cardiac insufficiency.

Said "indication" should be obtainable as clear measured results in numerical form which directly reflect the relevant condition of a patient and can directly guide physicians so that "stabilization of the patient" in the sense of an improvement in said measured values can be directly strived for as a primary aim of the therapy.

Said object is achieved according to the invention by a method for controlling the therapeutic treatment of a patient suffering from cardiac insufficiency, in which the manner in which the concentration of at least one of the vasoactive peptides adrenomedullin (ADM), endothelin-1 (ET-1) and/or vasopressin (AVP) changes in the blood of the patient after the beginning of a therapy is determined and, in the case of absence of a reduction or an insufficient reduction of said concentration, the therapeutic measures are assessed as unsatisfactory and the therapeutic measures are changed, whereas, in the case of a sufficient reduction in said concentration, a successful therapy is assumed.

More specific or preferred configurations of such a method comprise the measures stated in claims 2 to 13.

The vasoactive endogenous peptides to be determined by the method according to the invention are those whose secretion changes in a characteristic manner in the case of cardiac insufficiency. The vasoactive peptides belong either to endogenously formed vasodilatory or vasoconstrictive physiologically active peptides and are in particular the vasodilatory peptide adrenomedullin (ADM) and the vasoconstrictive peptides endothelin-1 (ET-1) and vasopressin (AVP). These are preferably determined with the use of assays of the applicant by means of which the liberation of the actual vasoactive peptides is determined by means of the determination of physiologically inactive copeptides (MR-proADM), CT-ProET-1), CT-proAVP or copeptin), which are determined like the vasoactive peptides from a respective propeptide precursor.

Their determination in relation to the control of therapy of the patients suffering from cardiac insufficiency can also be designated as the use as a short-term surrogate marker for the success of a therapy of cardiac insufficiency.

It is to be regarded as a use of the method according to the invention if the determination of the abovementioned peptides is supplemented by the determination of additional clinical or biochemical parameters, for example by additionally determining or concomitantly determining yet other endogenous vasoactive analytes. The peptides of the renin-angiotensin-aldosterone (RAA) system, in particular the vasoconstrictive peptide angiotensin II, the so-called substance P (SP) and furthermore the vasodilatory peptides $CGRP_{1-37}$, amylin (IAPP), endothelin-3 (ET-3) and the vasoactive intestinal peptide (VIP) may additionally be mentioned by way of example in this context. Taking into account further non-peptide analytes, such as NO (for example determinable as nitrite or nitrate), may furthermore be mentioned.

Where a determination of the respective analytes "in the blood" is mentioned, this term comprises the determination in whole blood, serum or plasma. The determination of the analytes is preferably carried out with the aid of immunodiagnostic assay methods in the form of immunoassays of the sandwich type, for example with one of the applicant's assays explained below.

The concentration of adrenomedullin (ADM) is preferably determined as the concentration of a midregional proADM fragment (MR-proADM) which comprises the amino acids 45-92 of preproadrenomedullin. A suitable assay is described in EP 1 488 209 B1 or WO 2004/090546 or in (2). With the use of this assay, normal ADM concentrations which are in the range of 0.2-0.6 nmol/l (the upper limit of the range is a threshold value which can be used as a guide for deciding on a therapy) are determined in healthy persons. The stabilization of a patient at such a normal concentration is the abovementioned primary therapeutic aim of the treatment of a cardiac insufficiency.

The concentration of endothelin-1 (ET-1) is preferably determined as the concentration of a C-terminal ET-1 fragment (CT-proET-1) which comprises the amino acids 168-212 of preproendothelin 1. A suitable assay is described in 1 564 558 B1 or WO 2005/078456 and in (3). With the use of this assay, normal ET-1 concentrations which are in the range of 25-70 pmol/l (the upper limit of the range is a threshold value which can be used as a guide for deciding on the therapy) are determined in healthy persons. The stabilization of the patient at such a normal concentration is likewise an abovementioned primary therapeutic aim of the treatment of a cardiac insufficiency.

For the determination of the concentration of vasopressin (AVP), the use of an assay with which the propeptide fragment CP-proAVP (copeptin) is determined and which is described in more details in the publication WO 2006/018315 or in (4) is recommended. With the use of this assay, normal AVP concentrations which are less than 13 pmol/l (<13 pmol/l) (said value is a threshold value which can be used as a guide for deciding on the therapy) are determined in healthy persons. The stabilization of a patient at such a normal concentration is a further primary therapeutic aim of the treatment of a cardiac insufficiency.

Taking into account only one of the abovementioned parameters, i.e. the stabilization of a patient at the normal concentration of only one of the abovementioned parameters, is sufficient to provide highly significant information for the success of a therapy or failure of a therapy, as will be shown below with reference to measured results in a Table 1.

As is also shown in below in a Table 2, the success of a treatment is indicated, but with a substantially higher significance, if it is simultaneously possible to bring two or preferably all three of said parameters into said normal ranges in a patient. This is because, although all parameters are found to be increased in the case of cardiac insufficiency, they are substantially independent of one another and can therefore supplement one another.

The in vitro determination according to the invention of one or more parameters can be carried out in routine clinical use in a manner expedient on a larger scale also as a simultaneous determination by means of a chip technology measuring apparatus or in the course of a so-called point-of-care (POC) determination using an immunochromatographic measuring apparatus. The determination and evaluation of the complex measured result of a multiparameter determination is effected in an expedient manner with the aid of a suitable computer program.

When the term "concentration" is used in this application, this term does not mean, in the sense of a limiting equivalence, only the stationary concentration of the actual vasoactive peptide which is measurable in the biological sample.

The most important pathophysiologically liberated vasoactive peptides discussed in the context of the present invention are present in biological fluids only to a relatively small extent in a freely measurable form or a form measurable in an unhindered manner. Substantial parts of the pathophysiologically liberated vasoactive peptides are rapidly withdrawn from the biological fluid by binding to receptors and other membrane or vascular structures and/or are degraded.

The measurement of inactive copeptides formed from the same precursor propeptides as is preferably effected according to the present invention with the use of the applicant's assays mentioned herein, reflects, in contrast to the instantaneous concentration in a biological fluid, the liberation of the vasoactive peptides in the sense of "active concentrations" over a relatively long time segment and permits indirect concomitant detection of bound or rapidly degraded fragments of the vasoactive liberated peptide too. In conjunction with the higher stability of such copeptides, this leads to higher measurable absolute concentration values for the analytes to be determined in the biological fluid, e.g. in serum or plasma.

The concentrations discussed in the present invention, however, are not necessarily only the measurable concentrations of such inactive copeptides but may also be the concentrations of other measurable analytes, for example small molecules, such as NO, which in each case are formed in a substantially proportional ratio to the concentrations measurable for said inactive copeptides or are present in the biological fluid. Such analytes present in a biological fluid (serum, plasma) in a proportional ratio to the vasoactive peptides or copeptides may be regarded as "surrogates of vasoactive peptides", the determination of which may be equivalent to the direct determination of the vasoactive peptides or the corresponding copeptides and in the same manner can give values which can optionally replace the measured values for the concentrations of the vasoactive peptides or of the copeptides in the present invention. The indirect determination of the vasoactive peptides by determining such "surrogates of vasoactive peptides" is intended to be included under the general term "determination of the concentration of vasoactive peptides".

In the case of diseases with a course which tends to be chronic without sudden deteriorations or improvements in the condition of the patient, as may be the case for a chronic cardiac insufficiency, there is, for example, a high probability that a steady overall state which is only slightly variable and changes only slowly will result with regard to the various disease-relevant analytes without therapeutic intervention or in the case of regular, constant therapeutic intervention by administration of medicaments. In such a case, the steady concentrations of an active analyte, in the present case of a vasoactive peptide, which are measurable in the biological fluid of the patient should be substantially proportional to the amounts of the same analyte which are pathophysiologically liberated over relatively long periods, as can be measured in the form of physiologically inactive copeptides by the applicant's assays. This means that deviations from the control values of healthy persons which can be determined in the preferred multiparameter determination of inactive copeptides according to the present invention and the cause of these deviations which is typical of the disease should also be reflected in the generally lower steady concentrations of the active analytes so that the specific choice of the measured "analyte concentrations" should not have a decisive qualitative influence on the diagnostic evaluations.

The invention is explained in more detail below in the experimental section with reference to two tables.

The measurements of MR-proADM, CT-proAVP and CT-proET-1 in patient plasmas, described in the experimental section, were effected by the applicant's assays which are mentioned further above and are described in the literature stated there and all of which essentially represent noncompetitive immunoluminometric sandwich assays.

Reference is made expressly to the general statements on the problem of determining ADM or ET-1 or AVP in patient samples and the explanations for carrying out the assays in said patents or the publications (2, 3, 4) for supplementing the statements in the present application.

The invention is explained in more detail below with reference to measured results for the markers ADM, ET-1 and AVP in patients suffering from cardiac insufficiency.

Experimental Section

Description of Assays

The measurement of MR-proADM in plasma was effected using an immunoluminometric sandwich assay substantially as described in the experimental section of the abovementioned WO 2004/090546 or in (2).

The measurement of CT-proET-1 in plasma was effected using an immunoluminometric sandwich assay substantially as described in the experimental section of the abovementioned WO 2005/078456 or in (3).

The measurement of CT-proAVP (copeptin) for determining AVP liberated in plasma was effected using an immunoluminometric sandwich assay substantially as described in the experimental section of WO 2006/018315 or in (4).

Collection of Measured Data:

For examining the question as to whether the determination of ET-1 (as CT-proET-1), ADM (as MR-proADM) and vasopressin (as CT-proAVP) alone or in combination is suitable for the early detection of the success of a therapy and hence for control of the therapy of patients suffering from cardiac insufficiency, a first blood sample was taken from all patients of a group of 377 patients who were admitted as emergencies with shortage of breath as the principle symptom, immediately after admission.

On the day of the emergency admission itself, therapeutic interventions were begun and a second blood sample was taken 4 days after the beginning of the intervention.

All patients were then observed over a period of 12 months, and the death of a patient or his rehospitalization owing to acute heart failure was recorded as a "event".

The group of patients consisted of 377 persons altogether, 288 male and 89 female. The average age was 67±11 years, the individual age of the persons being between 42 and 91 years. The assignment of the patients to the abovementioned NYHA classes was as follows:

NYHA I=21 patients; NYHA II=118; NYHA III=144; NYHA IV=94.

In the case of altogether 354 of the 377 patients, a value which was above said respective threshold value or normal range for healthy persons was measured on the day of admission for at least one of said markers.

Of these 345 patients (n=345), the 12 month mortality was 17% (59 patients), the 12 month rehospitalization (once or more frequently) was 20% (70 patients). This gives a total frequency of events of 38% (129 patients).

In the following table, the measured results obtained for the individual markers for patients with events (129 patients) on the day of emergency admission and on the fourth day thereafter (i.e. on day 4 after the beginning of the therapeutic intervention), are reproduced.

TABLE 1

| Marker/Measured value ranges | Number of patients n | Patients with at least 1 event in 12 months | % of patients with events |
|---|---|---|---|
| MR-proADM | | | |
| >0.6 nmol/l on day of admission | 340 | 129 | 37.9 |
| >0.6 nmol/l on day 4 | 156 | 125 | 80.1 |
| <0.6 nmol/l on day 4 | 184 | 4 | 2.2 |
| CT-proET-1 | | | |
| >70 pmol/l on day of admission | 331 | 126 | 38.0 |
| >70 pmol/l on day 4 | 141 | 120 | 85.1 |
| <70 pmol/l On day 4 | 190 | 6 | 3.2 |

TABLE 1-continued

| Marker/Measured value ranges | Number of patients n | Patients with at least 1 event in 12 months | % of patients with events |
|---|---|---|---|
| CT-proAVP | | | |
| >13 pmol/l on day of admission | 320 | 121 | 37.8 |
| >13 pmol/l on day 4 | 155 | 110 | 71.0 |
| <13 pmol/l on day 4 | 165 | 11 | 6.7 |

TABLE 2

| Taking into account the combined measured values on day 4 of | Number of patients n | Patients with at least 1 event in 12 months | % of patients with events |
|---|---|---|---|
| MR-proADM <0.6 nmol/l plus CT-proET-1 <70 pmol/l | 172 | 1 | 0.6 |
| Additionally taking into account CT-proAVP <13 pmol/l | 148 | 0 | 0 |

Table 1 (last column) shows that, when only a single marker is taken into account, a significant correlation is obtained between the event-free 12 month survival time and the normalization of the values for the respective marker after 4 days (only 2.2 or 3.2 or 6.7 events in the groups of "singly normalized patients").

Table 2 shows that the correlation is further considerably improved, a surprising event, if at the same time the measured results for MR-proADM and for CT-proET-1 are taken into account (only 0.6 event in the group of "doubly normalized patients"). If in addition CT-proAVP is taken into account as a third marker, a group of "triply normalized patients" is obtained, in which there were no events at all.

The physician can thus consider the normalization or at least reduction of the measured values for said markers as a short-term therapeutic aim of its therapeutic interventions. In this way, it was possible to distinguish rapidly, i.e. after only about 4 days (the period can also be shorter or longer) responders (who respond to the chosen therapy) from nonresponders (who do not respond to the chosen therapy) and, if appropriate, to initiate a change of therapy in the case of the nonresponders. Such an early adaptation of the therapy in the event of absence of therapeutic success, detectable from the measurable marker concentrations, can be life-saving or life-extending.

If the patient is resistant to therapy and responds to none of the chosen therapies, this may facilitate a rapid decision for more serious interventions, for example surgery.

REFERENCES

1. ALBERTUS BEISHUIZEN, KOEN J. HARTEMINK, ISTVAN VERMES, AB JOHAN GROENEVELD (2005), Circulating cardiovascular markers and mediators in acute illness: an update. Clinica Chimica Acta 354 (2005) 21-34
2. NILS G. MORGENTHALER, JOACHIM STRUCK, CHRISTINE ALONSO, ANDREAS BERGMANN, Measurement of Midregional Proadrenomedullin in Plasma with an Immunoluminometric Assay, Clinical Chemistry 51: 10, 2005, 1823-1829
3. JANA PAPASSOTIRIOU, NILS G. MORGENTHALER, JOACHIM STRUCK, CHRISTINE ALONSO, ANDREAS BERGMANN, Immunoluminometric Assay for Measurement of the C-Terminal Endothelin-1 Precursor Fragment in Human Plasma, Clinical Chemistry 52: 6, 2006, 1144-1151
4. NILS G. MORGENTHALER, JOACHIM STRUCK, CHRISTINE ALONSO, ANDREAS BERGMANN, Assay for the Measurement of Copeptin, a Stable Peptide Derived from the Precursor of Vasopressin, Clinical Chemistry 52: 1, 2006, 112-119
5. VAN CHENG, RADMILA KAZANAGAR, ALEX GARCIA, LESLIE LE-NERT, PADMA KRISHNASWAMY, NANCY GARDETTO, PAUL CLOPTON, ALAN MAISEL, A Rapid Bedside Test for B-Type Peptide Predicts Treatment Outcomes in Patients Admitted for Decompensated Heart Failure: A Pilot Study, J Am Coll Cardiol 2001; 37: 386-391

The invention claimed is:

1. A method for guiding non-surgical therapeutic treatment of a patient suffering from chronic cardiac insufficiency, said method comprising determining the concentration of at least two inactive peptides each of which is derived from the same propeptide precursor as a vasoactive peptides selected from the group consisting of adrenomedullin (ADM), endothelin-1 (ET-1) and vasopressin (AVP) in the blood of the patient before and after beginning therapy and comparing said before- and after-concentrations for each of said at least two inactive peptides wherein the at least two inactive peptides determined are selected from the group consisting of MR-proADM, CT-proET-1 and CT-proAVP, wherein no reduction of said concentrations indicates that the therapeutic measures are unsatisfactory and the therapeutic measures are changed, and wherein a reduction in said concentration indicates successful therapy.

2. The method according to claim 1, wherein said concentration is determined by means of an immunoassay in vitro in a whole blood, serum or plasma sample of the patient.

3. A method for guiding non-surgical therapeutic treatment options for a patient suffering from chronic cardiac insufficiency, comprising
   a) determining the concentrations of at least two inactive copeptides, each of which is formed from the same precursor as a vasoactive peptides selected from the group consisting of adrenomedullin (ADM), endothelin-1 (ET-1) and vasopressin (AVP) in the blood of the patient before therapy;
   b) determining the concentration of said at least two inactive peptides measured in step a), after beginning therapy;
   c) comparing the concentration of said at least two inactive peptides in the patient's blood before therapy to the concentration of said peptides after beginning therapy wherein the at least two inactive peptides determined are selected from the group consisting of MR-proADM, CT-proET-1 and CT-proAVP, wherein a reduction in the concentration of both of said peptides indicates that the therapy is effective and wherein no change or an increase in concentration indicates that the therapy is not effective.

4. The method according to claim 3, wherein the concentration of the at least two inactive peptides each of which is derived from the same propeptide precursor as a vasoactive peptides, is determined using an assay which determines the concentration of an inactive peptide formed from the same propeptide precursor as the vasoactive peptide.

5. The method of claim 3, wherein the concentration of the inactive peptide derived from the same propeptide precursor as ADM is determined using a sandwich immunoassay which permits the determination of the concentration of MR-proADM.

6. The method of claim 3, wherein the concentration of an inactive peptide derived from the same propeptide precursor as ET-1 is determined using a sandwich immunoassay which determines the concentration of CT-proET-1.

7. The method of claim 3, wherein the concentration of an inactive peptide derived from the same propeptide precursor as AVP is determined using a sandwich immunoassay which determines the concentration of CT-proAVP.

8. The method of claim 3 wherein a first measurement of the concentration of the at least two inactive peptides each of which is derived from the same propeptide precursor as the vasoactive peptides in the blood of the patient is made directly before the beginning of therapy and a second measurement is made within a period of 3 to 10 days after the beginning of the therapy.

9. The method of claim 8, wherein an insufficient reduction in the concentrations is present when the concentration of MR-proADM, is above a value of 0.6 nmol/l.

10. The method of claim 8, wherein an insufficient reduction in the concentrations is present when the concentration of CT-proET-lafter the beginning of therapy, is above a value of 70 pmol/l.

11. The method of claim 8, wherein an insufficient reduction in the concentrations is present when the concentration of CT-proAVP after the beginning of therapy, is above a value of 13 pmol/l.

12. The method of claim 3, wherein the reduction is regarded as sufficient and the therapy as successful if the concentration after the beginning of the therapy for CT-proET-1 and CT-proAVP are below 70 pmol/l and 13 pmol/l, respectively.

13. The method of claim 3, further comprising:
   d) repeating steps b), and c), when no change in the concentration of the at surrogate markers for the at least two vasoactive peptides is observed.

* * * * *

UNITED STATES PATENT AND TRADEMARK OFFICE
CERTIFICATE OF CORRECTION

PATENT NO. : 7,915,002 B2
APPLICATION NO. : 12/374757
DATED : March 29, 2011
INVENTOR(S) : Andreas Bergmann It is certified that error appears in the above-identified patent and that said Letters Patent is hereby corrected as shown below:

<u>Col. 8, Claim #1 – 5<sup>th</sup> Line</u> - *Sealed Patent reads "peptides"*
*HRFM Claim indicates - "peptide"*
*Patent should read "peptide" no "s" at the end*

<u>Col. 10, Claim #10 – 3<sup>rd</sup> Line</u> - *Sealed Patent reads "CT-proET-1after" no space before the word "after".*
*Patent should have a space before the word "after"*

Signed and Sealed this
Twenty-first Day of June, 2011

David J. Kappos
*Director of the United States Patent and Trademark Office*

UNITED STATES PATENT AND TRADEMARK OFFICE
CERTIFICATE OF CORRECTION

PATENT NO.       : 7,915,002 B2
APPLICATION NO.  : 12/374757
DATED            : March 29, 2011
INVENTOR(S)      : Andreas Bergmann It is certified that error appears in the above-identified patent and that said Letters Patent is hereby corrected as shown below:

Column 8, line 23 (Claim 1, line 5) -    *Sealed Patent reads "peptides"*
                                         *HRFM Claim indicates - "peptide"*
                                         *Patent should read "peptide" no "s" at the end*

Column 10, line 3 (Claim 10, line 3) -   *Sealed Patent reads "CT-proET-1after" no space*
                                         *before the word "after".*
                                         *Patent should have a space before the word "after"*

This certificate supersedes the Certificate of Correction issued June 21, 2011.

Signed and Sealed this
Twenty-sixth Day of July, 2011

David J. Kappos
*Director of the United States Patent and Trademark Office*